United States Patent [19]

Friend et al.

[11] Patent Number: 5,173,293

[45] Date of Patent: Dec. 22, 1992

[54] ANTI-T-CELL ANTIBODIES AS ADJUVANTS

[75] Inventors: Sherree L. Friend, Sunnyvale; Vernon T. Oi, Mountain View, both of Calif.

[73] Assignee: Becton Dickinson and Company, Franklin Lakes, N.J.

[21] Appl. No.: 314,731

[22] Filed: Feb. 23, 1989

[51] Int. Cl.$^5$ .................. A61K 39/02; A61K 39/12; A61K 39/395; G01N 33/531

[52] U.S. Cl. .................. 424/85.8; 424/88; 424/89; 424/92; 436/547; 436/548; 530/403; 530/405; 530/406; 530/806; 530/807; 530/808; 530/809; 530/387.3; 530/388.22; 530/388.75; 530/389.6; 530/391.7

[58] Field of Search .................. 424/85.8, 88, 89, 92; 435/7.24; 436/547, 548, 819; 530/389, 391, 403, 405, 406, 806–809

[56] References Cited

U.S. PATENT DOCUMENTS

| | | | |
|---|---|---|---|
| 4,433,059 | 2/1984 | Chang et al. | 436/512 |
| 4,381,292 | 4/1983 | Bieber et al. | 435/7.24 |
| 4,500,637 | 2/1985 | Neville, Jr. et al. | 435/2 |
| 4,520,110 | 5/1985 | Stryer et al. | 436/501 |
| 4,634,895 | 2/1987 | Casellas et al. | 424/85.91 |
| 4,659,678 | 4/1987 | Forrest et al. | 436/572 |
| 4,671,958 | 6/1987 | Redwell et al. | 424/85 |
| 4,696,980 | 6/1987 | Segal et al. | 424/85 |
| 4,741,900 | 5/1988 | Alvarez et al. | 424/85 |
| 4,950,480 | 8/1990 | Barber et al. | 424/85.8 |

FOREIGN PATENT DOCUMENTS

| | | |
|---|---|---|
| 0245078 | 11/1987 | European Pat. Off. |
| 0294703 | 12/1988 | European Pat. Off. |
| 644473 | 8/1984 | U.S.S.R. |
| 2188638 | 10/1987 | United Kingdom |
| 8805309 | 7/1988 | World Int. Prop. O. |

OTHER PUBLICATIONS

Kawamura & Berzofsky, J. Immunol., 136:58 (1986).
Kohler & Milstein, Nature, 256:495 (1984).
Jones et al., Nature, 321:522 (1986).
Klausner, BioTechnology, 6:773 (1988).
Lanzavecchia et al., Nature, 334:530 (1988).
Carayanniotis et al., Nature, 327:59 (1987).

*Primary Examiner*—David Saunders
*Attorney, Agent, or Firm*—Robert M. Hallenbeck

[57] ABSTRACT

An antigen/antibody complex is described wherein the antibody functions as an adjuvant. The antibody comprises an anti-lymphocyte antibody. The antigen comprises a hapten, peptide, protein, carbohydrate, virus, bacterium, parasite or other whole microorganism. The complex of antigen coupled to antibody may be used in immunizing a higher animal against an antigen.

20 Claims, 2 Drawing Sheets

ANTI-T-CELL ANTIBODIES AS ADJUVANTS

FIELD OF THE INVENTION

This invention relates to the use of adjuvants in the administration of vaccines, and more particularly relates to the use of anti-lymphocyte antibodies, especially anti-T cell antibodies, as adjuvants.

BACKGROUND OF THE INVENTION

Specific immunity can be enhanced by the use of adjuvants when administering antigen to a host. The immune response is mediated by a variety of cells in the immune system. There are two types of immune response: humoral immunity mediated by antibodies, and cellular immunity mediated primarily by cytotoxic T lymphocytes. Antigen presenting cells ("APC") process and present antigen to both B and T cells. B cells secrete specific antibodies as a result of activation and T cells either become helper cells to the humoral response or cytotoxic cells and directly attack the antigen. Adjuvants have been shown to augment these immune responses.

Initial presentation of an antigen induces both IgM and IgG antibodies, forming the primary response. This production of antibodies may fall off, however, over time. A secondary response, which principally involves the production of IgG antibodies, may be triggered by the secondary or later in time presentation of the antigen. A secondary or even primary response, however, is not guaranteed merely by priming the host with an antigen.

A difficulty often encountered in the administration of an antigen is the extent the immune system will respond. Certain antigens are not very immunogenic in that upon administration they provoke a weak primary response or no response at all. In such cases, the immune system may not respond to a secondary challenge, and for example, the host may suffer from the disease or condition that the immunization with the antigen was designed to prevent.

In such situations, it is common to give a biological response modifier ("BRM"). A BRM generally is defined as an immunopotentiating compound. It may be derived from bacteria, such as *Bordella pertussis* or *Corynebacterium parvum*. BRM also may include chemicals, such as polynucleotides, physiologically active molecules, such as thymic hormones, and adjuvants.

Adjuvants are compounds which enhance the immune systems response when administered with antigen producing higher antibody titres and prolonged host response. Commonly used adjuvants include Incomplete Freund's Adjuvant, which consists of a water in oil emulsion, Freund's Complete Adjuvant, which comprises the above with the addition of *Mycobacterium tuberculosis*, and alum. The difficulty, however, in using these materials in humans, for example, is that they are toxic or may cause the host to develop lesions at the site of injection.

This problem was recognized in EPA 87304005.9, published Nov. 11, 1987 ("Barber Application"). In the Barber Application, they sought to avoid the problem by coupling the antigen to a monoclonal antibody which was specific for a surface structure on "antigen presenting cells." APC generally consist of B cells and macrophages (but exclude T cells). Specifically, monoclonal antibodies directed against Class I and Class II cell surface MHC glycoproteins were described. These antibodies included anti-I-A and anti-I-E which were coupled to a variety of antigenic materials, including avidin, bovine serum albumin and strepavidin. The results suggested that antigens coupled to anti-Class I or Class II antibodies would provide a greater immune response than if the antigens had been presented without having been conjugated to the anti-Class I and anti-Class II antibodies. There was no suggestion that antibodies directed against non-MHC restricted structures might be used as adjuvants. Surprisingly, antibodies against cell surface structures other than those associated with Class I and Class II glycoproteins provide an enhanced immune response greater than that disclosed in the Barber Application.

Another approach was described by Kawamura and Berzofsky in J. Immunol., 136:58 (1986). In this approach, anti-Ig antibodies, which are reactive with immunoglobulins present on certain B cells, were conjugated to ferritin and myoglobin, and were administered to mice with Incomplete Freund's Adjuvant. Immunogenicity of the mixture was improved, but there was no indication of the immunogenicity of the mixture without the addition of the adjuvant.

SUMMARY OF THE INVENTION

This invention comprises an antibody/antigen complex which further comprises an antigen coupled or conjugated to an anti-lymphocyte antibody that reacts with cell surface molecules or structures other than Class I or Class II glycoproteins. The complex may be used in a host in order to provoke an immunizing response. The host immunized with the antigen/antibody complex includes higher animals, preferably comprises mammals, and most preferably comprises humans.

The anti-lymphocyte antibody may be polyclonal or monoclonal, and is preferably monoclonal. When it is monoclonal, it may be chimeric or mosaic. Alternatively, the antibody may be comprised of a fragment thereof such as Fab, Fab' or F(ab')$_2$. In all cases, the antibody may be IgG, IgA, IgD or IgM. Preferably, the antibody is IgG. The make-up of the heavy chain also may be of any isotype.

The anti-lymphocyte antibody coupled to an antigen to form an antigen/antibody complex then may be used in a host in order to provoke an immune response. The anti-lymphocyte antibody may be specific for surface structures on T cells, B cells, NK cells and macrophages but not for Class I or Class II APC associated cell surface structures. Preferably, the anti-lymphocyte antibody is an anti-T cell antibody. The anti-T cell antibody may be made against the CD3, CD4, CD5, CD8 or other structures on the surface of T cells.

The antigen to which the anti-lymphocyte antibody is coupled comprises peptides, haptens, carbohydrates, proteins, nucleic acids, viruses, bacteria, parasites and other whole microorganisms. Regardless of the antigen selected, it must be coupled to the antibody in such a way as not to interfere with the binding of the antibody to the lymphocyte. Binding the antigen to the Fc region of the antibody provides one possible site.

The antigen/antibody complex may be used as a vaccine to raise an immune response in the host. The complex initially may be given in an appropriate dosage in order to elicit an immune response. This may be followed by boosting with the complex or antigen alone. A variation of this approach may include the formation of one or more antibody/antigen complexes wherein one or more forms of an antigen are coupled to one or more antibodies and a plurality of such complexes is administered.

DETAILED DESCRIPTION

The present invention comprises a complex formed between an antigen and anti-lymphocyte antibody against a cell surface structure other than Class I or Class II glycoproteins. This antigen/antibody complex then may be administered to a host in order to elicit an immune response to the antigen administered. The purpose of administering the antigen/antibody complex is to provide protection to the host in the form of immunity to the antigen and to avoid the use of adjuvants which have undesired side affects.

In the preferred embodiment, the antibody is an anti-T cell antibody. It may be polyclonal or monoclonal, although monoclonal antibodies are preferred. Anti-T cell monoclonal antibodies, such as Leu-4 (anti-CD3), Leu-3a (anti-CD4) and Leu-2 (anti-CD8), are commercially available from Becton Dickinson Immunocytometry Systems (BDIS) or may be made to specific T cell surface antigens by any well known method, such as the method of Kohler and Milstein as described in Nature, 256:495 (1975).

Monoclonal anti-T cell antibodies may be made chimeric by the method of Morrison and Oi disclosed in U.S. Pat. Ser. No. 644,473, filed Aug. 27, 1984. Alternatively, the antibody made be made mosaic by the method of Winter disclosed in U.K. Pat. Appl. GB 2 188 638 filed Mar. 27, 1986, and also as described in Jones et al., Nature, 321:522 (1986). Chimeric antibodies are preferred.

In the preferred embodiment, the antigen may be as small as a hapten or may be as large as a whole organism, such as a virus or a portion thereof. The size and type of the antigen is not critical to the practice of this invention. Any antigen may be used for which an immune response is desired in a host. The invention is especially useful, however, for small weakly immunogenic haptens. The only limitation on the choice of antigen is that when the antigen/antibody complex is formed, the antigen binding site of the antibody is not hindered in any way such that binding of the antibody to the lymphocyte is significantly diminished.

The choice of antigen in this invention will depend on the immune response desired. For example, a response to the envelope glycoprotein, gp120, of HIV may be desired. That response could be achieved by coupling a pure preparation of gp120 to an anti-lymphocyte antibody or by coupling a fragment of the virus envelope to the anti-lymphocyte antibody and then administering the complex. In some circumstances, an immune response to more than gp120 may be desired, and several similar or related HIV cell surface antigens may be coupled to the same anti-lymphocyte antibody or to several different anti-lymphocyte antibodies. Again, using the HIV example, one might wish to use gp120 and gp40 as the antigens coupled to one or more anti-lymphocyte antibodies in order to try to elicit a more comprehensive response against HIV.

Coupling of the antibody to the antigen may be accomplished in one of several ways. Again, subject to the binding limitation in the preceding paragraphs, the choice of methods for conjugating antibody and antigen is not critical. One method includes sulfhydryl coupling, as described in U.S. Pat. Nos. 4,333,059, 4,671,958 and 4,741,900, for example. Briefly, the crosslinker molecule (e.g., SMCC [succinimidyl 4-(N-maleimide methyl) cytohexane-1-carboxylate]) is attached to the antibody via primary amines. Excess linker is removed and antigen with a free sulfhydryl adds to the maleimide portion of the linker.

Another method includes carbohydrate attachment to the Fc region of the antibody, as described in U.S. Pat. Nos. 4,671,958 and 4,741,900, for example. The sulfhydryl method is presently preferred.

Once the antigen/antibody complex or complexes are formed, the complex or complexes may be administered to the host. The administration regime need not differ from any other generally accepted vaccination programs. A single administration in an amount sufficient to elicit an effective immune response may be used. Alternatively, other regimes of initial administration of the complex followed by boosting with antigen alone or one or more complexes may be used. Similarly, boosting with either the complex or antigen may occur at times well after initial administration if antibody titres fall below acceptable levels.

EXAMPLE

The following antibodies against the mouse equivalent of T cell surface structures were used (the human equivalents, if any, are given in parentheses): (A) Lyt-2 (CD8); (B) Lyt-1 (CD5); (D) L3T4 (CD4). These antibodies are commercially available from BDIS. I-Ad is an anti-HLA-DR antibody similar to that used in the Barber Application. L160.3 is an irrelevant control.

The antibodies were conjugated to FITC (Research Organics) by placing antibody into a carbonate buffer at pH 9.5 and incubating it with FITC for 18 hours at 4° C. for 2 hours at 22° C. Excess FITC was removed by de-salting on a PD10 gel filtration column (Pharmacia) into PBS. Conjugation ratios were determined by measuring the optical density at 280 and 495 nm.

Once conjugated, 25 ug of complex was injected IP into a mouse. Eight mice were injected with each complex or with antibody and antigen alone, except that seven mice were injected with a complex formed with L160.3. Serum was collected on days 5, 8, 11, 16, and 26.

Serum was analyzed by radioimmunoassay for the production of anti-fluorescein antibodies in the mice. Antigen (in the form of ovalbumin fluorescein) was coated onto the wells of a polystyrene assay plate at a concentration of lug/well overnight at 4° C. or 2 hours at 22° C. Serum collected from each mouse was diluted into PBS containing 2% BSA and 0.2% $NaN_3$("RIA buffer") for testing. The assay plate was washed three times with RIA buffer. Sera and controls were added to each plate and incubated for 1 hour at 22° C. Excess sera was washed away with RIA buffer and anti-mouse Ig antibodies labelled with $125^I$ by the chloramine-T method were added to each well. The labelled solution of anti-mouse antibodies was incubated in each well for 1 hour at 22° C. The plate then was washed three times in RIA buffer. The individual wells were separated and counted in a gamma counter.

Figure 1A:
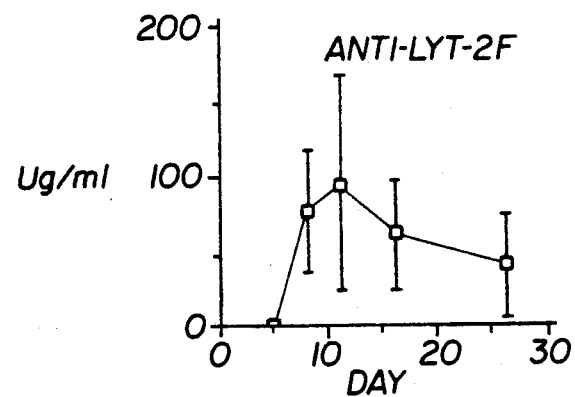
FIG. 1 comprises a plot of time (days) versus antibody concentration (ug/ml) for mice injected with fluorescein isothiocyanate (FITC) conjugated to: (A) Anti-Lyt 2; (B) Anti-Lyt 1; (C) Anti-Thy 1.2; (D) Anti-L3T4 and fluorescein (unconjugated); (E) Anti-L3T4; (F) Anti-L3T4 (mouse gamma 2b chimeric); (G) Anti-I-Ad; and (H) L160.3 (an irrelevant anti-human CD4 control).
Figure 1B:
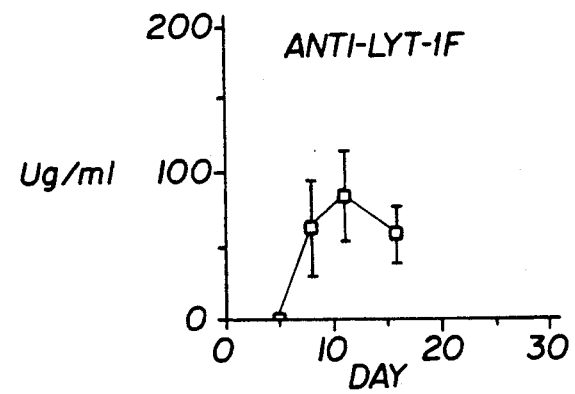
Figure 1C:
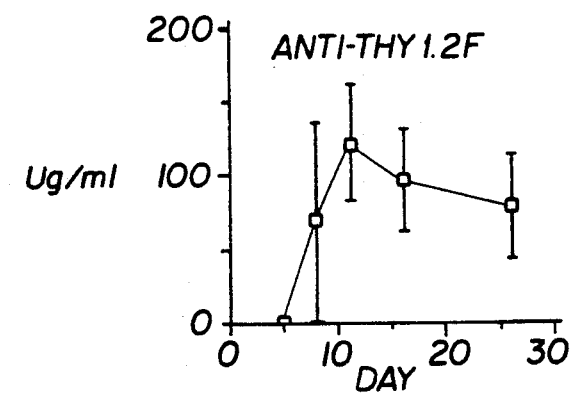
Figure 1D:
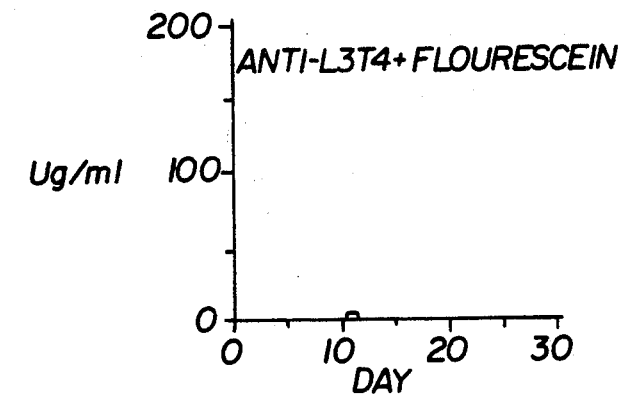
Figure 1E:
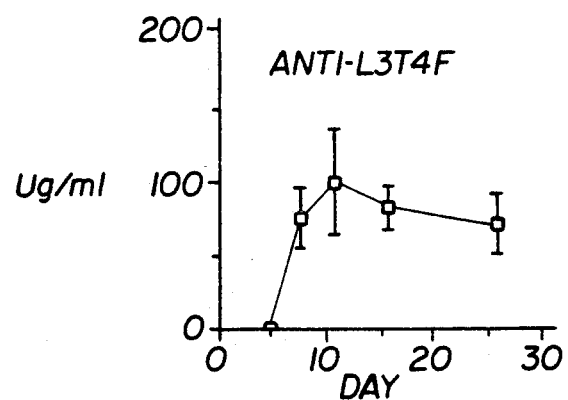
Figure 1F:
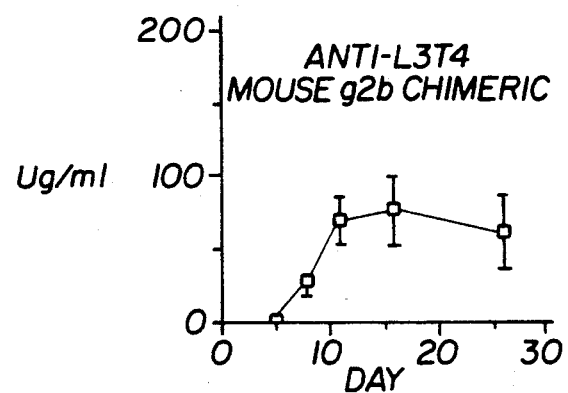
Figure 1G:
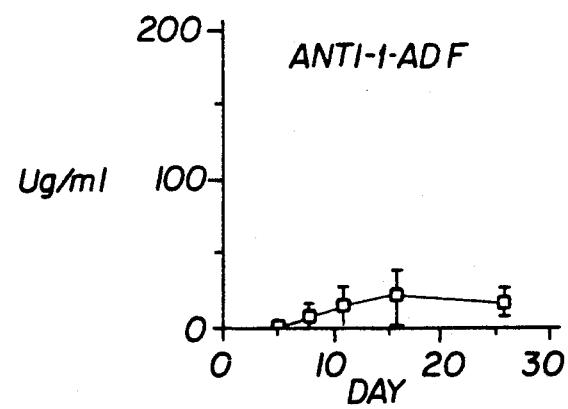
Figure 1H:
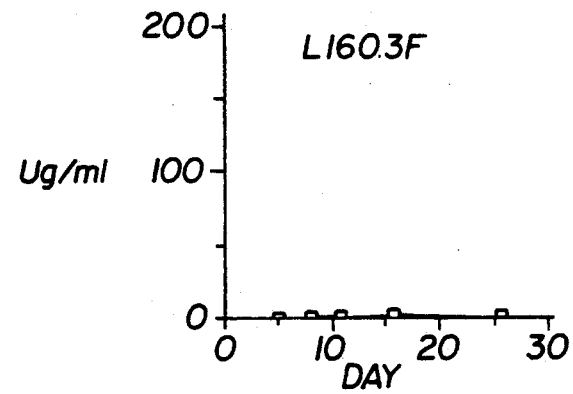

Referring to FIG. 1, all of the mice given an antigen/antibody complex formed between anti-lymphocyte antibodies and fluorescein (i.e., FIGS. 1A, B, C, E and F) showed a marked immune response to fluorescein by the production of anti-FITC antibodies. The response to a complex formed between L160.3 and FITC essentially was non-existent (FIG. 1H). Similarly, the immune response to the complex formed between anti-J Ad (which is the same as the anti-APC antibody described in the Barber Application) and FITC was statistically less than the response seen when an anti-T cell antibody was used in the complex (FIG. 1G). There was no response in mice when fluorescein and antibody were administered together but unconjugated (FIG. 1D).

Accordingly, the use of an anti-lymphocyte antibody coupled to an antigen of the type described herein to elicit an immune response in a host is a surprising and significant improvement over the art. It now appears possible to raise an immune response against previously non-immunogenic or weakly immunogenic antigens without the complications introduced by other known BRM.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for immunizing a host against an antigen by administering to said host an effective amount of an antigen/antibody complex formed between an anti-T cell antibody and said antigen wherein the antibody recognizes a cell surface structure other than MHC Class I or Class II glycoproteins and wherein said complex is formed by conjugating or coupling said antibody to said antigen.

2. The method of claim 1, wherein the anti-T cell antibody is selected from the group consisting of anti-CD3, CD4, anti-CD5 and anti-CD8 antibodies.

3. The method of claim 1 wherein the antibody is monoclonal.

4. The method of claim 3 wherein the antibody is chimeric.

5. The method of claim 1 wherein the antigen is selected from the group consisting of haptens, carbohydrates and peptides larger than haptens, and whole microorganisms.

6. The method of claim 5 wherein the antigen is a hapten.

7. The method of claim 5 wherein the whole microorganism is a virus.

8. The method of claim 5 wherein the antigen is a peptide larger than a hapten.

9. The method of claim 5 wherein the antigen is a protein.

10. The method of claim 5 wherein the antigen is a carbohydrate.

11. The method of claim 5 wherein the whole microorganism is a parasite.

12. The method of claim 5 wherein the whole microorganism is a bacteria.

13. The method of claim 1 wherein the host is a mammal.

14. The method of claim 13 wherein the host is a human.

15. The method of claim 1 wherein the administration of the complex is followed by the administration of antigen alone at a later time.

16. The method of claim 1 wherein the administration of the complex is followed by the administration of the complex at a later time.

17. The method of claim 1 wherein an effective amount of a plurality of complexes is administered.

18. The method of claim 17 wherein each of the complexes differs in the antibody coupled to the antigen.

19. The method of claim 17 wherein each of the complexes differs in the antigen coupled to the antibody.

20. The method of claim 17 wherein each of the complexes differs in both the antibody and antigen.

* * * * *